United States Patent [19]

Bergeron

[11] Patent Number: 5,496,839
[45] Date of Patent: Mar. 5, 1996

[54] ANTI-NEOPLASTIC, ANTI-VIRAL AND RIBONUCLEOTIDE REDUCTASE ACTIVITY AFFECTING PHARMACEUTICAL COMPOSITIONS AND METHODS OF TREATMENT

[75] Inventor: Raymond J. Bergeron, Gainesville, Fla.

[73] Assignee: University of Florida Research Foundation, Inc., Gainesville, Fla.

[21] Appl. No.: 475,690

[22] Filed: Jun. 7, 1995

Related U.S. Application Data

[62] Division of Ser. No. 376,889, Jan. 20, 1995, which is a division of Ser. No. 299,126, Sep. 2, 1994, which is a division of Ser. No. 124,557, Sep. 22, 1993, Pat. No. 5,391,563, which is a division of Ser. No. 993,620, Dec. 21, 1992, Pat. No. 5,292,775, which is a division of Ser. No. 645,644, Jan. 25, 1991, Pat. No. 5,173,505, which is a division of Ser. No. 313,734, Feb. 22, 1989, Pat. No. 5,128,353, which is a continuation-in-part of Ser. No. 746,672, Jun. 20, 1985, abandoned.

[51] Int. Cl.⁶ .............. A01N 43/36; A01N 43/38; A01N 43/76; A61K 31/40

[52] U.S. Cl. .............. 514/374; 514/375; 514/408; 514/411; 514/422; 514/423

[58] Field of Search .............. 514/408, 411, 514/422, 423, 374, 375

[56] References Cited

U.S. PATENT DOCUMENTS

| | | | |
|---|---|---|---|
| 5,128,353 | 7/1992 | Bergeron | 514/374 |
| 5,173,505 | 12/1992 | Bergeron | 514/374 |
| 5,292,775 | 3/1994 | Bergeron | 514/374 |
| 5,391,563 | 2/1995 | Bergeron | 514/374 |

*Primary Examiner*—Nathan M. Nutter
*Attorney, Agent, or Firm*—Kerkam, Stowell, Kondracki & Clarke; Dennis P. Clarke

[57] ABSTRACT

A method for treating a human or non-human animal afflicted with malignant cells sensitive to parabactin or a pharmaceutically acceptable salt or complex thereof comprising administering to the animal an amount of parabactin effective to inhibit the proliferation of the malignant cells.

2 Claims, No Drawings

ANTI-NEOPLASTIC, ANTI-VIRAL AND RIBONUCLEOTIDE REDUCTASE ACTIVITY AFFECTING PHARMACEUTICAL COMPOSITIONS AND METHODS OF TREATMENT

The invention described herein resulted in part from research conducted under NIH Grant No. R01 AM29936. The United States Government has certain rights in and to the invention described and claimed herein.

RELATED APPLICATIONS

This is a division of application Ser. No. 08/376,889 filed Jan. 20, 1995, which is a division of application Ser. No. 08/299,126 filed Sep. 2, 1994, which is a division of application Ser. No. 08/124,557 filed Sep. 22, 1993 (now U.S. Pat. No. 5,391,563 issued Feb. 21, 1995), which is a division of application Ser. No. 07/993,620 filed Dec. 21, 1992 (now U.S. Pat. No. 5,292,775 issued Mar. 8, 1994), which is a division of application Ser. No. 07/645,644 filed Jan. 25, 1991 (now U.S. Pat. No. 5,173,505 issued Dec. 22, 1992), which is a division of application Ser. No. 07/313,734 filed Feb. 22, 1989 (now U.S. Pat. No. 5,128,353 issued Jul. 7, 1992), which is a continuation-in-part of application Ser. No. 06/746,672 filed Jun. 20, 1985 (now abandoned).

BACKGROUND OF THE INVENTION

1. Field of the Invention

The present invention relates to certain novel anti-neoplastic, anti-viral and ribonucleotide reductase catalytic activity affecting pharmaceutical compositions and methods of treatment.

2. Prior Art

Due to the critical role played by iron in the function of a variety of biological redox systems, e.g., ribonucleotide reductase, electron transport proteins, iron flavorproteins, hydroperoxidase and oxygenases, life, with the possible exception of the lactobacilli, without iron is essentially unknown.

Microorganisms are particularly sensitive in their iron requirement and many have evolved remarkable mechanisms for iron acquisition. They synthesize low molecular weight, virtually ferric ion specific chelators, i.e., siderophores which assist transport of exogenous iron into the cell where it is utilized in supporting growth [Neilands, Ann. Rev. Biochem. 50, pp. 715–731 (1981); Bergeron, Chem. Rev. (in press) (1984); Emery, Metal Ions in Biological Systems, pp. 77–121 (1973)]. Many of these chelators are relatively simple molecules consisting of catechol moieties (e.g., 2,3-dihydroxybenzoyl groups) attached to various amine backbones. All of these ligands bind iron tenaciously; e.g., parabactin, a siderophore synthesized by the plant pathogen, *Paracoccus denitrificans* [Tait, Biochem. 146, pp. 191–197 (1975)], forms a 1:1 metal complex with an iron formation constant in the order of $10^{48}$ moles/1.

Although certain microbes can interchangeably utilize the siderophores of other prokaryotes, this ability is not universal. It has recently been shown, for example, that parabactin cannot be utilized by large numbers of bacterial pathogens [Bergeron et al, Antimicrob. Agents and Chemo. 24, pp. 725–730 (1983)]. In fact, the siderophore exhibits potent bacteriostatic and fungistatic effects and appears to act by competing with microbes for available iron.

Weinberg [Nutrition and Cancer 4, pp. 223–233 (1983) and Physiological Reviews 64, pp. 65–96 (1984)] has provided a compelling rationale for iron-withholding as a strategy against infection and neoplasia. Porter et al [Cancer Research 42, pp. 4072–78 (1982)] has shown that $N^1$, $N^8$-dihydroxybenzoylspermidine demonstrates significant cytotoxicity to L1210 cells (50% growth-inhibitory dose, 10 µM) and postulates that the activity is probably attributable to its iron-chelating properties. However, not all iron chelators exhibit cytotoxicity.

It is an object of the present invention to provide certain anti-neoplastic, anti-vital, anti-psoriasis, anti-malarial and ribonucleotide reductase activity affecting pharmaceutical compositions and methods of treatment wherein the active agent is one of a small class of specific iron chelators.

SUMMARY OF THE INVENTION

The present invention provides pharmaceutical compositions in unit dosage form adapted for administration to a human or non-human animal comprising a) an anti-neoplastic, anti-viral, anti-psoriasis, anti-malarial or ribonucleotide reductase activity affecting, effective amount of a compound of the formula:

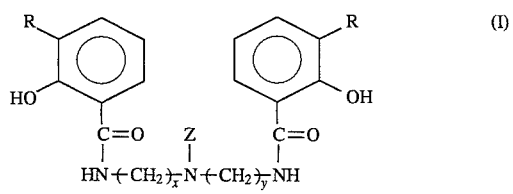

or

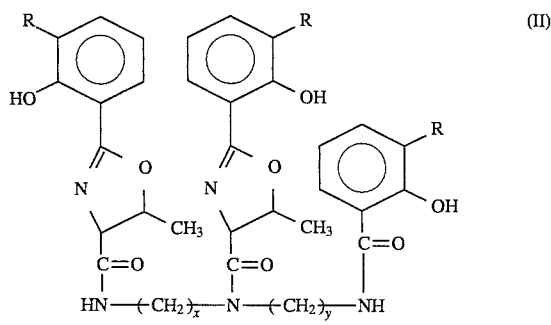

Wherein:

Z is

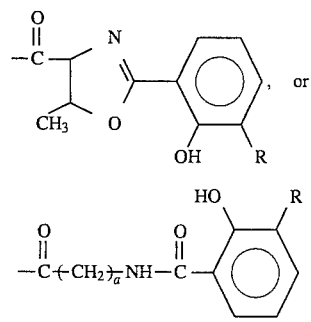

R is H or OH, x is 3 or 4, y is 3 or 4, and a is 1, 2 or 3, or a salt or complex thereof with a pharmaceutically acceptable ion or ligand, and b) a pharmaceutically acceptable carrier therefor.

The present invention also provides methods for treating human or non-human animals afflicted with malignant cells comprising administering thereto an anti-neoplastic effective amount of a compound of formula I or II.

The present invention also provides methods for treating human or non-human animals afflicted with a ribonucleotide reductase dependent vital infection comprising administering thereto an anti-vital effective amount of a compound of formula I or II.

The present invention further provides a method for affecting the catalytic activity of a ribonucleotide reductase in a human or non-human animal, comprising administering thereto a ribonucleotide reductase activity affecting amount of a compound of formula I or II.

The present invention also provides a method for treating human or non-human animals afflicted with psoriasis comprising administering thereto an effective anti-psoriasis amount of a compound of formula I or II.

The present invention additionally provides a method for treating human or non-human animals afflicted with malaria comprising administering thereto an effective amount of a compound of formula I or II.

DETAILED DESCRIPTION OF THE INVENTION

Preferred among the compounds of formula I as active agents in the pharmaceutical compositions and methods of treatment of the present invention are those having the formula:

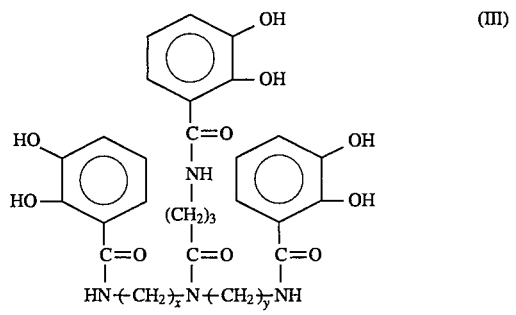

wherein x and y have the meanings set forth above.

Particularly preferred is the compound of formula III wherein x is 3 and y is 4.

Also preferred among the compounds of formula I are those having the formula:

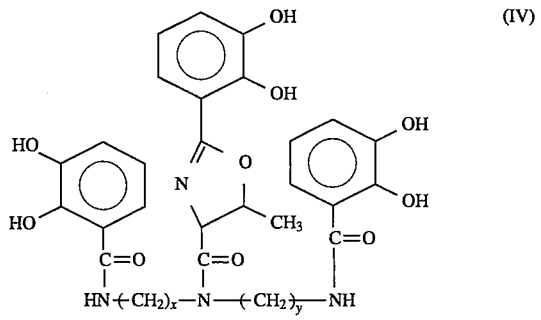

wherein x and y have the meanings set forth above.

Particularly preferred among the compounds of formula IV is that wherein x is 3 and y is 4.

Preferred among the compounds of formula II are those having the formula:

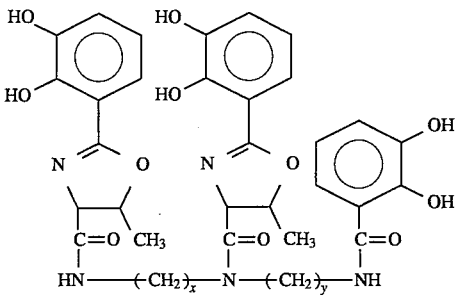

wherein x and y have the meanings set forth above.

Particularly preferred is the compound of formula V wherein x is 3 and y is 4. Also particularly preferred are the compounds of formula V wherein x is 4 and y is 3 and where both x and y are 3.

The compounds of formulas I and II may be prepared according to the methods described in Bergeron et al, Synthesis, pp. 698–692 (1982); Bergeron et al, J. Org. Chem., 45, pp. 1589–1592 (1980); Bergeron et al, J. Med. Chem. 23, pp. 1130–1134 (1980); Bergeron et al, J. Org. Chem. 46, pp. 4524–4529 (1983); Bergeron et al, J. Org. Chem. 48, pp. 3432–3438 (1983); Bergeron et al, J. Org. Chem. 46, pp. 3712–3718 (1981), the disclosures of each of which are incorporated by reference herein.

The pharmaceutical compositions of the invention preferably contain a pharmaceutically acceptable carrier suitable for rendering the compound or mixture administrable orally as a tablet, capsule or pill, or parenterally or transdermally. The active ingredients may be admixed or compounded with any conventional, pharmaceutically acceptable carrier. It will be understood by those skilled in the art that any mode of administration, vehicle or carrier conventionally employed and which is inert with respect to the active agent may be utilized for preparing and administering the pharmaceutical compositions of the present invention. Illustrative of such methods, vehicles and carriers are those described, for example, Remington's Pharmaceutical Sciences, 4th Ed. (1970), the disclosure of which is incorporated herein by reference. Those skilled in the art, having been exposed to the principles of the invention, will experience no difficulty in determining suitable and appropriate vehicles, excipients and carriers or in compounding the active ingredients therewith to form the pharmaceutical compositions of the invention.

The therapeutically effective amount of active agent to be included in the pharmaceutical composition of the invention depends, in each case, upon several factors, e.g., the type, size and condition of the animal, the disorder to be treated, the intended mode of administration, the capacity of the animal to incorporate the intended dosage form, etc. Generally, an amount of active agent is included in each dosage form to provide from about 50 to about 500 mg, preferably from about 50 to about 250 mg.

The active agent employed in the pharmaceutical compositions and methods of treatment of the invention may comprise a pharmaceutically acceptable salt or complex of the compounds of formulas I or II, e.g., sodium, potassium or other non-toxic metal salts, amine salts, etc.

The compound, compositions and method of the invention are useful for the treatment of a wide variety of disorders. Exemplary of such disorders are leukemias, solid tumors and other cancers, ribonucleotide reductase dependent viruses, i.e., DNA viruses, e.g., herpes, etc.

Those skilled in the art will be aware that the amounts of the various components of the compositions of the invention to be administered in accordance with the method of the invention to a patient will depend upon those factors noted above.

Generally, however, amounts of active agent are administered to provide dosages thereof from about 50 to about 500 mg/kg, preferably from about 50 to about 250 mg/kg, the frequency of administration and duration of treatment being dependent upon the type and nature of the animal and disorder treated.

The invention is illustrated by the following non-limiting example.

EXAMPLE

Murine L1210 leukemia cells were maintained in logarithmic growth as a suspension culture in RPMI 1640 containing 2% HEPES-MOPS buffer and 10% fetal calf serum as described by Porter et al, Science 219, pp. 1083–1085 1983). Cultures were treated while in logarithmic growth (0.5 to $1\times10^5$ cells/ml) with the test compounds at concentrations ranging from $10^{-6}$ to $10^{-2}$M. After 24 to 48 hours, cells were counted by electronic particle analysis and viability determinations with trypan blue. Total iron content of the medium was determined by atomic absorption analysis.

All compounds tested were initially screened for anti-vital activity against herpes simplex I, KOS strain or vesicular stomatitis virus in CV-1 monkey kidney cells using a methyl cellulose disk overlay assay as described by Schroeder et al, J. Med. Chem. 24, pp. 1078–1983 (1981). The inhibition of virus replication was determined quantitatively by measuring the amount of virus produced by infected cells during a single cell cycle of infection, in the presence of the compound tested. CV-1 cells were infected with 20 PFU/cell of herpes simplex virus. One hour post infection, cells were rinsed with Modified Eagle's Medium and exposed for 30 min. to a medium composed of 1% anti-herpes rabbit antiserum to neutralize unpenetrated virus. The cells were rinsed once with medium and then cultured with the test compound. A baseline used for measuring net virus production was obtained by harvesting and freezing one sample which was untreated 4 hours after infection. The remaining samples were collected and frozen 18–20 hours post infection. Virus was titrated in CV-1 cells by a plague assay as described by Hughes et al, J. Virol. 16, pp. 275–283 (1975). In studies designed to prevent the anti-vital activity of the chelators, $FeCl_3$ at various concentrations was added to medium containing a fixed concentration of the test compounds and the anti-vital assay performed as described above.

The partition equilibrium values for octanol and phosphate buffered saline were determined for certain of the test compounds. The compounds were added in nitrogen saturated methanol at the same concentration to three acid washed test tubes and the alcohol evaporated leaving a thin film of compounds coating the interior of the tube. Next, 5 ml each of degassed phosphate buffered saline (pH 7.4) and n-octanol were added. The tubes were sealed with Teflon caps under argon and rotated at 6 rpm at 27° C. for 12 hours. Samples were removed from the n-octanol and PBS layers and measured for the various compounds by observing the samples absorbance at the appropriate wavelength; parabactin, 333 nm; GABA, 330 nm; Compound II, 329 nm; and dihydroxybenzoic acid, 319 nm. Absorbance values were compared to Beer's Lambert's plots generated for each compound.

The effectiveness of the test compounds as inhibitors of cell growth or vital replication was assessed according to the drug concentration required to reduce cell growth or vital plaque formation by 50% ($IC_{50}$). Against L1210 leukemia, all of the spermidine catecholamides were active in the micromolar range with parabactin and GABA being the most effective at 2 µM (see Table I). The catecholamides were even more active against the DNA virus, herpes simplex type I, inhibiting replication at concentrations ranging from 0.4 µM (parabactin) to 5 µM. By contrast, they were totally inactive against the RNA virus, vesicular stomatitis, at concentrations up to 1 µM.

TABLE I

In Vitro Antileukemic and Antiviral Activity of Spermidine Catecholamides and Related Compounds

| Polyamine Derivative | Formation Constant (moles/l) | Antileukemic Activity ($IC_{50}$, 48 hr) | Antiviral Activity Herpes simplex I ($IC_{50}$) | Antiviral Activity Vesicular stomatitis[+] ($IC_{50}$) |
|---|---|---|---|---|
| N-benzylspermidine | 0 | 4.0 mM | 1 mM | 1 mM |
| 2,3-dihydroxybenzoic acid (DHBA) | $10^{36}$ | 2.8 mM | 1 mM | 1 mM |
| $N^1,N^8$-bis(2,3-dihydroxybenzoyl)-$N^4$-threonyl-spermidine | $10^{40}$ | 14.0 µM | 55.0 µM | 1 mM |
| $N^1,N^8$-bis(2,3-dihydroxybenzoyl)-spermidine (Compound II) | $10^{40}$ | 7.0 µM | 32.0 µM | 1 mM |
| $N^1,N^8$-bis(2,3-dihydroxybenzoyl)-$N^4$-(4-[2,3-dihydroxybenzamido]-butyryl) spermidine (GABA) | $10^{45}$ | 2.0 µM | 18.0 µM | 1 mM |
| N-[3-(2,3-dihydroxybenzamido)propyl]-N-[4-(2,3-dihydroxybenzamino)-butyryl]-2-(2-hydroxyphenyl)trans-5-methyl-oxazoline-4-carboxamide (Parabactin) | $10^{48}$ | 2.0 µM | 0.4 µM | ND** |
| N-[3-(2,3-dihydroxybenzamido)propyl]-1,3-bis(2,3-dihydroxyphenyl)-trans-5-methyl-2-oxazoline-4-carbonamido]propane (Vibrobactin) | $10^{48}$ | 2.0 µM | ND** | ND** |

**Not determined
[+]Estimated by methyl cellulose disk overlay assay [Schroeder et al, J. Med. Chem. 24, pp. 1078–1083 (1981).

The compound appears to be non-toxic to the monkey kidney cell monolayers used in the plaque inhibition assay at concentrations which fully inhibited herpes replication. In fact, when resting cell monolayers were treated for 24 hours with 100 μM Compound II and then replaced in drug-free media, their growth was identical to that of untreated cells.

When the compounds were ranked according to their estimated iron binding constants (Table I), the order generally paralleled both the anti-leukemic and anti-herpetic activities of the compounds. The simple bidentate parent ligand DHBA displayed minimal activity, while $N^4$-benzyl-spermidine, which has no iron chelating potential, was virtually inactive in either system. This suggests that the spermidine moiety of the siderophores was not responsible for their activities. Furthermore, the effects of the ligands could be prevented by addition of ferric chloride, supporting the idea that iron chelation is the source of activity. Both the anti-leukemic activity and the anti-herpetic activity of Compound II were fully attenuated by the inclusion of exogenous iron in the incubation media (Table II). Similar results were also obtained with parabactin in the herpes replication assay.

While not wishing to be bound by any theory as to the mechanism of the action of the active ingredients of the invention, it is hypothesized that the activities of the compounds are not only related to the ability to sequester iron but to the ability of nonchelated siderophores to diffuse across the plasma membrane. As has been shown by Raymond and co-workers, [J. Amer. Chem. Soc., 100, pp. 5362–5370 (1978)], the rate of removal of iron from transferrin by catecholamide iron ligands is quite slow. Considering that a vast majority of iron in tissue culture media (8 μM) is bound to transferrin, it is reasonable to postulate that the catecholamides can exist for some time in the media in a free state, during which time they may diffuse into cells at rates associated with favorable partition coefficients.

TABLE II

Prevention of the Anti-leukemic and Anti-herpetic Activities of Compound II with Fe (III)

| System | Compound II (μM) | (FcCl) (μM) | % Control |
|---|---|---|---|
| L1210 growth | 10 | 0 | 23 |
| | 10 | 4 | 64 |
| | 10 | 8 | 96 |
| | 10 | 12 | 104 |
| Herpes replication | 100 | 0 | 0 |
| | 100 | 9 | 20 |
| | 100 | 19 | 53 |
| | 100 | 38 | 138 |

The partitioning of various chelators between n-octanol and phosphate buffered saline is indicated in Table III. It should be noted that the ratios of ligand partition coefficients (catecholamide/DHBA) are closer to the ratios of the chelator's anti-leukemic activity than are the ratios of the binding constants (Table I). The best example is seen when comparing the activity of parabactin with DHBA. Although parabactin is 1012 times more effective at binding iron than DHBA, it is only $10^3$ times more active as an antineoplastic. However, the ratio of their partition constants between octanol and phosphate buffered saline is much closer to their biological activity ratios $10^{1.7}$. Similar results are obtained when comparing the activities of each of the other chelators relative to their partition coefficients indicating that cell penetration as well as ion-chelation potential may determine catecholamide activities.

TABLE III

Partition Coefficients and $G^°_{transfer}$ Determined in: Phosphate Buffered Saline (PBS) pH = 7.40; n-octanol Mixture

| Chelator | Solubility in PBS | Conc. n-Octanol Conc. PBS | $G^°_f$ $^{Kcal M-1}$ |
|---|---|---|---|
| DHBA | 1.30 × 10 M | 0.07 | +1.57 |
| Compound II | 2.55 × 10 M | 0.97 | −0.04 |
| Parabactin | 1.29 × 10 M | 32.44 | −2.06 |

The selective effect on the iron chelators on DNA (but not RNA) virus replication strongly suggests that they are affecting ribonucleotide reductase, a rate-limiting enzyme in DNA synthesis which catalyzes the conversion of ribonucleotides to deoxyribonucleotides. The enzyme consists of two subunits, one of which is heme-containing and essential to function [Thelander et al, Ann. Rev. Biochem. 48, pp. 133–158 (1979)]. Precedent for such drug action is provided by the anticancer agent, hydroxyurea, which inhibits cell growth by interfering with ribonucleotide reductase via a free radical scavenger mechanism involving the iron moiety of the enzyme [Thelander et al, supra; Laniken et al, J. of Virol. 41, pp. 893–900 (1979)].

It is well-known that malignant cells require DNA to divide and that if such a cell cannot generate sufficient DNA, it will eventually die. The enzyme ribonucleotide reductase is required to manufacture the deoxyribonucleotide precursors in the malignant cell for DNA manufacture. The compounds of formulas I and II above inhibit ribonucleotide reductase and therefore are cytotoxic for a wide variety of malignant cells. [Ganeshagurn et al, Biochemical Pharmacology, Vol. 29, pp. 1275–1279 (1980); Bergeron et al, Biochem. and Biophys. Res. Comm., Vol. 121, pp. 848–854 (1984); Bergeron et al, J. Med. Chem., Vol. 23, pp. 1130–1133 (1980); Sato et al, Cancer Research, Vol. 41, pp. 1637–1641 (1981); Elford Biochem. and Biophys. Res. Comm., Vol. 33, pp. 129–135 (1968); Lederman et al, Blood, Vol. 64, pp. 748–758 (1984)].

Most importantly, the compounds of the invention show little, if any, toxicity to normal cells, further underscoring their value as broad spectrum anti-neoplastic agents.

It should also be noted that the active ingredients of the present invention are more effective anti-neoplasts and anti-vital agents than Compound II which was previously disclosed by Porter et al, supra. The difference in activity is associated with-the enhanced lipophilicity and iron binding ability of the active agents of the invention.

The $IC_{50}$ values at which the present chelators inhibited growth of L1210 cells and replication of herpes virus are in the range of anti-neoplastic and anti-vital agents being used clinically. For example, the anti-herpetic agents, 2-fluoro-5-iodo-I-B-D-arabinofuranosylcytosine (known as FIAC) and acyclovir, have $IC_{50}$ values of 0.6 and 40 μM, respectively, in an in vitro system using the same herpes strain but a slightly different (vero) monkey kidney cell line [DeClercq, Antimicrob. Agents and Chemo. 212, pp. 661–663 (1982)].

The compounds of formula I and II have also been found to be effective anti-psoriasis agents. As described hereinbefore, these compounds inhibit cellular proliferation at the ribonucleotide reductase level. Ribonucleotide reductase is an iron-dependent enzyme controlling the rate limiting step of DNA synthesis, and is greater than 95% inhibited by the above compounds at micromolar concentrations. Because psoriatic tissue is rapidly proliferating tissue and is highly dependent on ribonucleotide reductase, the compounds described herein are active anti-psoriasis agents.

Research leading to the present invention was supported by Grants NIAMDD (AM-29936), CA-33321 and CA-22153 from the National Cancer Institute and by the Veterans Administration. The U.S. Government has certain rights in this invention.

The compounds of formula I and II have also been found to be effective anti-malarial agents. While not wishing to be bound by any theory as to the anti-malarial mechanism of the compounds, it is hypothesized that the activity is somehow predicated on the heavy metal chelating properties of the compounds. The following example illustrates the anti-malarial aspects of the invention.

EXAMPLE 1

The anti-malarial activity of the compounds listed in Table IV were determined using the method of Scheibel et al, Mol. Pharmacol., 20, pp. 218–223 (1981).

In this study, *Plasmodium falciparum* were grown in petri dishes using the conventional candle jar technique (Jensen, J. B., and W. Trager. *Plasmodium falciparum* in culture; use of outdated erythrocytes and description of the candle jar method. J. Parasitol. Vol. 63, pp. 883–886 (1977). Parasites were grown for 24 hours in 1.5 ml petri dishes in a candle jar before exposure to the chelators of interest. The *Plasmodium falciparum* were next exposed to various concentrations of the ligands, and $ED_{50}$ values determined after two and three days of exposure. Although all of the ligands were active, parabactin was the most active at day two with an $ED_{50}$ of 2.6 µM while vibriobactin was the most active chelator at three days with an $ED_{50}$ of 1.8 µM.

TABLE IV

| Concentration (in µM) required to reduce in vitro growth of *P. falciparum* 50% ($ED_{50}$) after exposure for 2 days and 3 days | |
|---|---|
| | Day 2 | Day 3 |
| Vibriobactin | 4.5 | 1.8 |
| Parabactin | 2.6 | 2.3 |
| Compound II | 4.5 | 3.7 |
| GABA | 5.1 | 4.3 |

As is apparent from the results in Table IV, all of the compounds are active anti-malarial agents.

I claim:

1. A pharmaceutical composition in unit dosage form adapted for administration to a human or non-human animal comprising a) an anti-malarial effective amount of a compound of the formula:

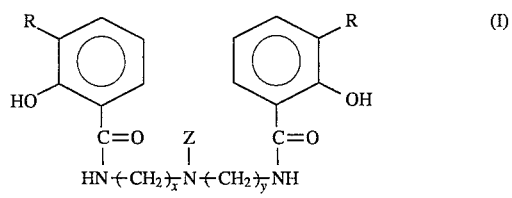

or

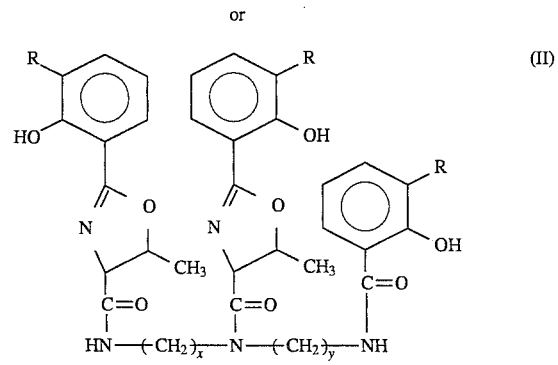

Wherein:

Z is

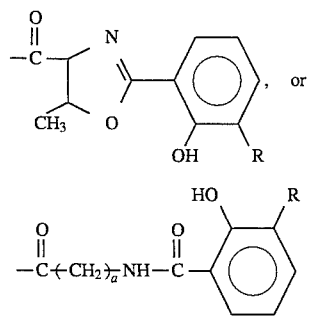

R is H or OH, x is 3 or 4, y is 3 or 4, and a is 1, 2 or 3, or a pharmaceutically acceptable salt or complex and b) a pharmaceutically acceptable carrier therefor.

2. A pharmaceutical composition according to claim 1 wherein said compound is parabactin.

\* \* \* \* \*